(12) United States Patent
Tesse

(10) Patent No.: US 10,668,043 B2
(45) Date of Patent: Jun. 2, 2020

(54) POTENTIATED ANTIMICROBIAL AGENTS

(71) Applicant: SEPTEOS, Paris (FR)

(72) Inventor: Nicolas Tesse, Vaucresson (FR)

(73) Assignee: SEPTEOS, Paris (FR)

( * ) Notice: Subject to any disclaimer, the term of this patent is extended or adjusted under 35 U.S.C. 154(b) by 218 days.

(21) Appl. No.: 15/510,988

(22) PCT Filed: Sep. 15, 2015

(86) PCT No.: PCT/EP2015/071093
§ 371 (c)(1),
(2) Date: Oct. 6, 2017

(87) PCT Pub. No.: WO2016/041958
PCT Pub. Date: Mar. 24, 2016

(65) Prior Publication Data
US 2018/0021296 A1    Jan. 25, 2018

(30) Foreign Application Priority Data

Sep. 15, 2014 (FR) .................................. 14 58663
Dec. 9, 2014 (FR) .................................. 14 62136

(51) Int. Cl.
| | | |
|---|---|---|
| A61K 31/34 | (2006.01) | |
| A61K 31/4178 | (2006.01) | |
| A61K 31/43 | (2006.01) | |
| A61K 31/424 | (2006.01) | |
| A61K 45/06 | (2006.01) | |
| A61K 31/09 | (2006.01) | |
| A61K 31/351 | (2006.01) | |
| A61K 9/00 | (2006.01) | |
| A61K 31/352 | (2006.01) | |
| A61K 31/496 | (2006.01) | |
| A61K 31/65 | (2006.01) | |
| A61K 31/7036 | (2006.01) | |

(52) U.S. Cl.
CPC ............ *A61K 31/34* (2013.01); *A61K 9/0053* (2013.01); *A61K 31/09* (2013.01); *A61K 31/351* (2013.01); *A61K 31/352* (2013.01); *A61K 31/4178* (2013.01); *A61K 31/424* (2013.01); *A61K 31/43* (2013.01); *A61K 31/496* (2013.01); *A61K 31/65* (2013.01); *A61K 31/7036* (2013.01); *A61K 45/06* (2013.01); *Y02A 50/481* (2018.01)

(58) Field of Classification Search
CPC ...... A61K 31/09; A61K 31/34; A61K 31/351; A61K 31/352; A61K 31/4178; A61K 31/424; A61K 31/43; A61K 31/496; A61K 31/65; A61K 31/7036; A61K 9/0053; A61K 45/06
See application file for complete search history.

(56) References Cited

U.S. PATENT DOCUMENTS

| | | |
|---|---|---|
| 3,787,566 A | 1/1974 | Gauvreau |
| 2006/0134237 A1 | 6/2006 | Greene et al. |
| 2008/0214518 A1 | 9/2008 | Remmal |

FOREIGN PATENT DOCUMENTS

| | | |
|---|---|---|
| WO | WO 99/66796 A1 | 12/1999 |
| WO | WO 2006/120567 A2 | 11/2006 |

OTHER PUBLICATIONS

Definition of prevent, Oxford English Dictionary Online, http://dictionary.oed.com/, accessed online Mar. 27, 2010, especially definition 9a. at p. 2. (Year: 2010).*
The Merck Manual, www.merckmanuals.com, Last full review/revision Sep. 2008, accessed online on Nov. 12, 2014 (Year: 2014).*
Foreign priority document France 1458663, received at WIPO Nov. 5, 2015 (Year: 2015).*
Abd El-Kalek et al., "Synergistic Effect of Certain Medicinal Plants and Amoxicillin Against Some Clinical Isolates of Methicillin-Resistant *Staphylococcus aureus* (MRSA)," International Journal of Pharmaceutical Applications, vol. 3, Issue 3, 2012, pp. 387-398.

(Continued)

*Primary Examiner* — Jonathan S Lau
(74) *Attorney, Agent, or Firm* — Birch, Stewart, Kolasch & Birch, LLP

(57) ABSTRACT

The object of the invention is to provide a potentiated antimicrobial agent for use in treating a microbial infection, characterized in that the antimicrobial agent is used in combination with a compound of the following formula I:

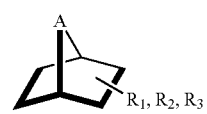

(I)

in a compound of formula (I): antimicrobial agent mass ratio, ranging from 8:1 to 1:10 and in that the microbial infection is induced in particular by a strain A pathogen and in that on this strain A, the concentration of compound (I) meets the following equation:

$[C] < [MIC]/x$ where [C] is the concentration according to the invention of compound (I) to be used on the strain A
[MIC] is the MIC measured for the compound (I), alone, on this strain A x is higher than or equal to 100, advantageously to 1 000, more advantageously x is between 2 000 and 10 000, or even higher than 50 000.

14 Claims, 2 Drawing Sheets

(56) References Cited

OTHER PUBLICATIONS

Bachir et al., "Antibacterial Activity of the Essential Oils from the Leaves of Eucalyptus globulus against *Escherichia coli* and *Staphylococcus aureus*," Asian Pacific Journal of Tropical Biomedicine, vol. 2, No. 9, 2012 (published online Sep. 28, 2012), pp. 739-742.
Fawad et al., "Antimicrobial Activity of Eucalyptus Tereticornis and Comparison with Daily Life Antibiotics," International Journal of Pharmaceutical Sciences Review and Research, vol. 12, Issue 1, Article-004, Jan.-Feb. 2012, pp. 21-29.
French Preliminary Search Report for French Application No. 1458663, dated Feb. 26, 2015.
French Preliminary Search Report for French Application No. 1462136, dated Apr. 2, 2015.
Hendry et al., "Antimicrobial Efficacy of Eucalyptus Oil and 1,8-cineole Alone and in Combination with Chlorhexidine Digluconate Against Microorganisms Grown in Planktonic and Biofilm Cultures," J. Antimicrobial Chemotherapy, vol. 64, No. 6, Dec. 2009 (Adv. Acc. Pub. Oct. 16, 2009), pp. 1219-1225.
International Search Report and Written Opinion of the International Searching Authority (Forms PCT/ISA/210, PCT/ISA/237 and PCT/ISA/220) for International Application No. PCT/EP2015/071093, dated Dec. 2, 2015.
Jedličková et al., "Antibacterial Properties of the Vietnamese Cajeput Oil and Ocimum Oil in Combination with Antibacterial Agents," Journal of Hygiene, Epidemiology, Microbiology and Immunology, vol. 36, No. 3, 1992, pp. 303-309.
Marei et al., "Comparative Antifungal Activities and Biochemical Effects of Monoterpenes on Plant, Pathogenic Fungi," Pesticide Biochemistry and Physiology, vol. 103, No. 1, 2012 (published online Mar. 28, 2012), pp. 56-61.
Marinas et al., "Rosmarinus officinalis Essential Oil as Antibiotic Potentiator Against *Staphylococcus aureus*," Biointerface Research in Applied Chemistry, vol. 2, Issue 1, 2012 (published online Feb. 15, 2012), pp. 271-276.
Mulyaningsih et al., "Synergistic Properties of the Terpenoids Aromadendrene and 1,8-cineole from the Essential Oil of Eucalyptus globulus Against Antibiotic-Susceptible and Antibiotic-Resistant Pathogens," Phytomedicine, vol. 17, No. 13, Nov. 2010, pp. 1061-1066.

* cited by examiner

POTENTIATED ANTIMICROBIAL AGENTS

The object of the invention is the compounds of formula (I), used at a dose at which they do not have antimicrobial properties any longer, for use as agents for potentiating the antimicrobial active ingredients with which they are co-administrated. In particular, the "potentiator(s)+antimicrobial(s)" combination has the purpose of preventing and/or treating bacterial and fungal infections in humans or animals.

The invention relates also to a process for potentiating antimicrobials wherein one or more compounds of formula (I) are co-administrated with said antimicrobial. In this process, the compound of formula (I) is used at a dose at which it is inactive alone.

OBJECT OF THE INVENTION

Background

The invention relates to providing solutions to problems related to activity decrease or loss of antimicrobials during their period of commercial and medical use. The invention is thus a solution applicable to current antimicrobials and which will be applied to future antimicrobials.

Following the advent of antimicrobials in the 1940', it turned out soon that microbes (bacteria and fungi) had the capacity to adapt to antimicrobials which were used. The efficiency thereof decreases over time and throughout their use. 2 strategies exist to fight against resistance, the discovery of new antimicrobial molecules on the one hand, and the combination with molecules which selectively block resistance mechanisms on the other hand.

For about twenty years, a decrease in the number of new antimicrobial molecules entering the market has been observed, which caused a major increase in the global prevalence of resistant microbes. As a result, there is a complex situation for patients which are treated with more difficulty for their microbial infections.

Description

The invention describes the use of compounds of formulae (I) to potentiate antimicrobials. Unexpectedly, these compounds have demonstrated their ability to potentiate the effect of antimicrobials at low doses (from 0.01 to 100 mg/l) very far from those for which they can, alone, have antimicrobial properties. Consequently, the antimicrobials with which the compounds of formulae (I) are co-administrated have, because of potentiation, an activity higher than that usually observed.

The invention aims at potentiating <<antimicrobials>>, usable in humans or animals and not all the compounds which have <<antimicrobial properties>>, which in turn are often not administrable to humans or animals because of too high a toxicity or too high an antimicrobial activity threshold requiring doses incompatible with health.

It is important to remind that any molecule has, in the absolute, antimicrobial properties. The antimicrobial properties of a molecule have thus to be assessed with regard to the minimum concentration which inhibits the bacterium.

The invention is based on the surprising discovery that compounds, which have antimicrobial properties at very high doses (level incompatible with a use in medicine to that end) and with minimum inhibitory concentrations (MIC) higher than 5 000 mg/L, advantageously higher than 10 000 mg/L, have potentiating effects at low doses (0.01 to 100 mg/l). At these doses, it becomes contemplatable to use compounds (I) in humans or animals.

Still also surprisingly, it has been observed that the potentiating effect is better at a low dose of the compound (I), and that the effect (for compounds having antimicrobial properties at very high doses) increases when departing from the dose at which the compound (I) has alone antimicrobial properties.

For example, it has been unexpectedly noticed that cineole, which has antimicrobial properties at a concentration in the order of one g/L (MIC of 25 000 mg/L to 50 000 mg/L that is 2.5 to 5%, depending on the strains), has potentiating effects on antibiotics at these concentrations close to the MIC (1 to 3 dilutions).

When its concentration is decreased below the MIC, cineole does not potentiate antibiotics any longer (see examples 2 and 6). Then, very surprisingly, it has been noticed that by further significantly decreasing the concentration of cineole, by 10 to 50 times less than the MIC, cineole has again potentiating effects on a very great number of antibiotics on a very great number of strains, this time at doses compatible with medical use.

A great advantage is that compounds (I) used at doses far from their efficiency threshold, are most often usable in humans or animals without toxicity requirements because of the absence of toxicity or at acceptable toxicity levels. This would not be the case if it were desirable to use them at the high doses at which they have antimicrobial properties or even at doses close to their MIC at which they could potentiate antimicrobials.

Still as surprisingly, the potentiating effect observed with the compound according to the invention is not specific to a particular resistance mechanism but is observed on various strains, regardless of whether they developed or not one or more distinct resistance mechanisms.

Prior Art

Figure 1:
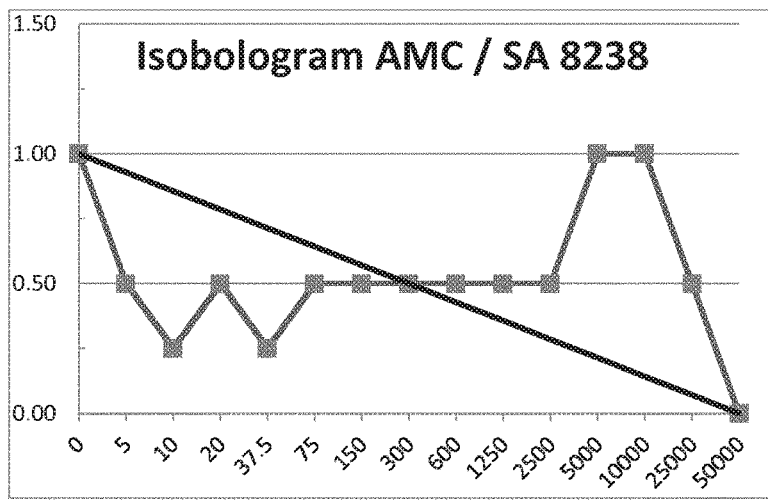
FIG. 1 is an isobologram revealing the amoxicillin MIC curve observed as a function of concentration (dilution) of cineol (strain: SA8238).

Prior art describes in many publications the antimicrobial properties of some compounds (I). These publications do not anticipate the potentiating effect of the compounds (I) at doses for from their efficiency threshold.

Prior art is significant on the compounds (I) because they belong to chemical classes which are well investigated in numerous fields. The compounds (I) within the scope of the present invention have the following characteristics which make it possible to depart them from prior art and which make it possible to contemplate their use as potentiators of antimicrobials administrated to humans and animals:

A/ they are used at low doses (0.01 to 100 mg/l), which doses are far from their antimicrobial properties threshold, their potentiating effect is not specific to particular action or resistance mechanisms.

B/ They have been validated by screening methods adapted to their physico-chemical characteristics.

C/ They have, at doses in which they potentiate, an effect/toxicity ratio which allows a safe use in humans or animals.

D/ They make up one or more isolated chemical entity(ies) with characteristics that are reproducible constantly to infinity because the method for obtaining them (synthesis, hemi-synthesis, extraction) permits it.

E/ They do not have a particular toxicity which would prohibit their use even at a low dose (genotoxicity, cardiotoxicity, . . . )

A/Regarding the Activity Levels Measured in Prior Art

In prior art, the concentration used to observe an antimicrobial activity is not compatible with a future use in humans or animals, in particular for a systemic application. In most of scientific publications, the medical use is contemplated whereas the efficient concentrations measured (in the order of several mg/ml) are incompatible with this use. The antimicrobial effects measured have very often been measured for contents of essential oil, or its active ingredient, in the order of several mg/ml. But, such a concentration is not suitable for a future use in humans or animals, in particular systemically. 1 mg/ml corresponds to 1 g/l or 1 g/kg or even 0.1%. If the MIC were 1 mg/ml, depending on the pharmacokinetics parameters, at least 1 g/kg/d live weight should be administrated. For example, the efficient dose for a cow should be at least 500 g/d and at least 60 g/d for humans (this corresponds to the minimum dose because it is assumed here that the product is fully absorbed and distributed in the organism). These far too high doses are not contemplatable for a safe use in therapeutics.

For example, two publications can be mentioned which mention the antibacterial effect of terpenoids and their possible capacity of potentiating antimicrobials:

Biointerfacae Vol 2, Issue 1, 2012, 271-276: Marinas and al: *Rosmarinus officinalis* essential oil as antibiotic potentiator against *Staphylococcus aureus*. If this publication seems to be close to the invention, it is important to note the contemplated eucalyptol dose (p274) which, at 25 µL/mL (that is 25 ml/L that is 25 g/l) is very far from the dose administrable to humans or animals. The synergy test contemplated is made with the storage solution (50% cineole) that is 50 g/L, higher than the MIC of cineole in the publication, which dosage is incompatible with a use in medicine.

Journal of Antimicrobial Chemotherapy (2009) 64, 1219-1225: Hendry et al: Antimicrobial efficacy of eucalyptus oil and 1,8-cineole alone and in combination with chlorhexidin digluconate against microorganisms grown in planktonic and biofilm cultures.

Once again, the synergy is contemplated with a product which has antimicrobial properties. The concentration of cineole contemplated is 4 g/L, which dose is very close to the MIC of cineole in the publication (8-64 g/L) but too high to be contemplatable in a human or animal administration.

Clearly, the invention is to be differentiated from both these publications because in the same, the doses contemplated are very high whereas the concentration contemplated is in proximity of the MIC.

B/Regarding Maladjustment of the Methods Described in Prior Art

The authors that have worked according to different approaches (active ingredients alone, natural products, . . . ) on the chemical families comprising the compounds (I) have generally used the standard antibacterial effect measurement methods without adapting them to the hydrophobic volatile nature of terpenoids and phenylpropanoids.

For example, WO 99/66796 (Wisconsin Alumni Research Foundation) describes a method for sensitising microbial cells to antibacterial compounds comprising a step of contacting an antibacterial compound with a sesquiterpenoid, to improve the effect of the antibacterial compound.

In this application, the MICs have been determined with the disc diffusion method, inappropriate to the volatile and hydrophobic nature of the compounds (I) and related families. This method consists in depositing paper discs impregnated with known amounts of compounds to be tested onto an agar medium seeded with the bacterium to be investigated. A concentration gradient of the compound appears on the agar medium around each disc; after 18 hours, the inhibition halo diameter is measured. This method is however not reliable for hydrophobic compounds which, because of very different surface tensions and contact angles on hydrophilic surfaces, interfere with the formation of the concentration gradient in the agar medium. In some zones, the concentration of compounds to be tested is much higher than the theoretical concentration. Thus, the tests cannot be quantitative, whereas they can be qualitative. Further, a dilution of the hydrophobic compound to be tested is noted in ethanol, without however correcting the result whereas ethanol is an antibacterial and a volatile compound.

It is to be noted that this application teaches that no effect is obtained with terpenes different from sesquiterpenes.

C/Regarding the Toxicity of Compounds of Prior Art

As regards natural compounds and compositions, there is some confusion between the natural origin and the absence of toxicity. Essential oils (and derivative thereof) are usually described as being of a low toxicity, which is often true in food applications or in perfumery but mistaken within the scope of a therapeutic administration.

As regards isolated chemical compounds, the confusion also exists and relates to the natural origin (extraction) of the compounds.

For example, WO2006/120567 (Advanced Scientific developments) describes pharmaceutically compositions comprising at least one active therapeutic substance described as being not toxic, chosen from carveol, thymol, eugenol, borneol, carvacrol, alpha-ionone, beta-ionone, and isomers, derivatives and mixtures thereof, and comprising, as a second active therapeutic substance an antibiotic. Carveol, thymol, eugenol, borneol, carvacrol, alpha-ionone, and beta-ionone, used alone, have an antibacterial activity and a number of them however raise toxicity problems as well, which are ignored in this application.

For example, carvacrol has the following toxicity data: LD 50 (mouse, intravenous) is 80 mg/kg whereas the lowest letal dose orally is 100 mg/kg, in two mammal species (cats and rats). These data are to be compared with the 0.3 mg/ml (that is 300 mg/kg) dose, contemplated in the document.

D/Regarding the Chemical Variability of the Compounds Described in Prior Art

The use of essential oil is an issue, in industrial scale, in terms of quality and reproducibility given that the composition of an essential oil varies from batch to batch.

For example DE 196 31 037 (Boehringer) describes the use of a tea tree essential oil to potentiate the effect of antibiotics on *Staphylococcus aureus* strains. The main component, the tea tree essential oil, is terpinen-1-ol.

This variability has especially three consequences which limit the industrialization in view of an application in humans or animals:

it is difficult to ensure consistency of therapeutic effect it is difficult to ensure low toxicity of the products the cost related to supplying and quality and reproducibility management of materials is important.

The following table lists the teaching of these prior arts:

TABLE 1

| | A/Active products at contemplated dose | B/Screening method incompatible with the chemical nature of the compounds | C/Toxicity at the contemplated dose | D/Chemical variability problem | Contemplated dose |
|---|---|---|---|---|---|
| Marinas et al | Yes | Yes | Yes | No | 15 g/L that is 15 000 mg/l |
| Hendry et al | Yes | No | Yes | No | 4 g/L that is 4 000 mg/l |
| WO2009/043987 Aromatechnologies | Yes | Yes | Yes | Yes | 0.1 to 0.4% that is: 1 to 4 000 mg/L |
| WO2006/120567 Advanced | Yes | Yes, (no dispersing agent) | Yes | No | 0.3 mg/ml that is 3 000 mg/l |
| DE 19631037 Boehringer | Yes | No (milk test) | Yes | Yes | 1 to 2 mg/ml that is 1 000 to 2 000 mg/l |
| WO 99/66796 Wisconsin Alumni | Yes | Yes | Yes | No | 1 mM that is 222 mg/L (for sesquiterpenoids) |
| Present Invention | No | No | No | No | 0.01 to 100 mg/L |

The work relating to the compounds (I) at low doses far from those to which they have an antimicrobial activity is novel and prior art has not, to our knowledge, contemplated this use.

Definitions

By "micro-organism", it is intended any living organism, which is invisible to the naked eye because of its low dimensions.

By "organism", it is meant any animal or plant biological entity (living being) capable of being born, being developed and normally breeding.

In this patent, the microbe definition takes up the micro-organism definition, limited to the medical field to which the invention refers. Thus, the "microbes" are potentially pathogenic living microorganisms (bacteria, fungi, yeast and mycobacteria). The term thus excludes inert pathogens such as viruses and prions.

By "antimicrobial", it is intended any compound for being administrated to humans or animals capable of killing or inhibiting microbe growth. Pharmaceutically acceptable salts of these antimicrobials are also included within this definition. This includes, for example, sodium, potassium, calcium salts, etc. and amino salts of procaine, dibenzylamine, ethylenediamine, ethanolamine, methylglucamine taurine, etc., as well as the acid addition salts such as hydrochlorides and basic amino acids. The term thus gathers antibiotics (their combinations with resistance mechanism inhibitors), antifungals for a systemic or local use.

By "antimicrobial properties", it is meant the properties of any substance capable of destroying or inhibiting microbe growth. Products which have antimicrobial properties comprise in particular antimicrobials and biocides.

In contrast to the term "antimicrobial", which gathers antibacterials, antifungals for being administrated, the term "biocide" gathers products having antimicrobial properties for being applied to inert systems (viruses and prions).

By "antibacterial properties" and "antifungal properties", it is intended not only bactericide and fungicide properties characterized by the destruction of bacteria and fungi (and yeasts, mycobacteria), but also bacteriostatic and fungistatic properties, characterized by growth inhibition of said bacteria and fungi (and yeasts, mycobacteria). Products which have antibacterial or antifungal properties comprise in particular antimicrobials.

By antibiotic "resistant bacterium", it is intended, within the purposes of the present invention, a bacterium resistant to at least one, in particular at least two, in particular at least three, or even at least four, antibiotic(s) or antibiotic family(ies), conventionally used.

By "multi-resistant bacterium", it is intended, within the purposes of the present invention, a bacterium resistant to several antibiotics, in particular for which the strain should be sensitive, or a priori sensitive, more particularly a bacterium which has at least two non-natural resistances.

"Natural resistances" and "acquired resistances" are distinguished. Some antibiotics have never been efficient, at non-toxic doses, against some bacterial strains or species. This is a natural resistance. When normally efficient antibiotics turn out to be not or not much efficient towards a bacterium, this bacterium has developed an acquired resistance.

A "microbial infection" within the purposes of the present invention designates an infection caused by one or more microbial strains and includes phases from host colonisation to pathologic phases. The phrase "microbial infection" thus encompasses any detrimental effect, clinic sign, symptom or any disease appearing in humans or animals following colonisation by the microbe.

By "terpenoid", it is intended according to the invention any compound comprising a backbone close to a terpene. A "terpene" designates an isoprene derivative which is obtained in a biological way by the condensation of C5 units, resulting for example in monoterpenes, sesquiterpenes. By "close to", it is intended that the backbone is similar to a terpene or different in that at least one alkyl substituent, normally present, can be absent or carried by another atom. The backbone can further be substituted with various radicals such as saturated or unsaturated, linear or cyclic aliphatic radicals (alkyls, alkenyls, alkylenes), oxy, aldehydes, esters, alcohols, ethers or sulphur or nitrogen equivalents thereof. The terpenoid can advantageously be of a natural origin.

By "phenylpropanoid", it is intended according to the invention any compound comprising a backbone close to a phenylpropane. A "phenylpropane" designates a derivative obtained by biological synthesis from phenylpropane and resulting in C6 (aromatic)-C3 (aliphatic) or C6 (aromatic)-C1 (aliphatic) derivatives and to corresponding lactones. By "close to", it is intended that the backbone is similar to a phenylpropane, in particular the phenyl unit is included, or different in that at least one alkyl substituent, normally present, can be absent or carried by another atom. The backbone can further be substituted by various radicals such as saturated or unsaturated, linear or cyclic aliphatic radicals (alkyls, alkenyls, alkylenes), oxy, aldehydes, esters, alcohols, ethers and sulphur or nitrogen equivalents thereof. The phenylpropanoid can advantageously be of a natural origin.

The term "prophylaxis" or "preventing an infection" such as used in the present application designates any delaying degree in the onset of clinic signs or symptoms of infection, as well as any inhibition degree in the severity of clinic signs or symptoms of infection, including but not limited to, the total prevention of said infection. This requires that the antimicrobial and the compound according to the invention are co-administrated to humans or animals likely to be colonised by a microbial strain for preventive purposes, for example following a surgery, implantation of a medical device or an intrusive medical act. This prophylactic administration can take place before, during or after the act likely to cause an infection (in particular a nosocomial infection) for the purpose of preventing, improving, and/or reducing the severity of any subsequent infection.

The term "treatment" for the purposes of the present invention implies that the antimicrobial and the compound according to the invention are co-administrated to a subject (human or animal) at the time of colonisation or after the contamination or the contamination suspicion by a microbial strain likely to cause an infection such as a nosocomial infection. The term "treatment" or "treating an infection" thus includes:
   any curative effect (growth inhibition or microbe destruction) achieved by virtue of the antimicrobial+compound according to the invention co-administration as well as the improvement in clinic signs or symptoms observed as well as the improvement of the subject condition;
   slowing, interrupting, as well as stopping infection progression. The antimicrobial-compound according to the invention co-administration can indeed also make it possible to slow down the progression of a microbe and/or fully or partially prevent a microbial infection from being extended to surrounding tissues and beyond;
   inhibition, attenuation or prevention of detrimental consequences of the infection such as cellular or physiological damage caused by toxins produced by some microbes at the infected or neighbouring tissues.

The term "co-administrated" means that the antimicrobial (or the antimicrobial mixture) and the compound according to the invention (or the compound mixture according to the invention) are administrated in a combined or juxtaposed form to the subject (man or animal). The combination includes any drug combination, any pharmaceutical composition, any pharmaceutical kit, and any drug comprising (i) at least one antimicrobial and (ii) at least one compound according to the invention. Compounds (i) and (ii) can be present in the form of a mixture or in the form of distinct formulations or compositions in said combination. The combination can also comprise several antimicrobials, for example 2, 3, 4 or more antimicrobials, and/or several compounds according to the invention, in particular 2, 3 or more compounds according to the invention. These components form a functional unit because of a common indication, which is the implementation of an antimicrobial treatment. This combination therapy is more specifically intended to prophylaxis and/or treatment of microbial origin infections and diseases, in particular nosocomial infections.

The co-administration can be simultaneous or spread over time.

The term "simultaneous" means that the antimicrobial (or the antimicrobial mixture) and the compound according to the invention (or the compound mixture according to the invention) are administrated in the meantime, at the same time, to a subject (man or animal). These compounds can be administrated in the form of a mixture or, simultaneously but separately, in the form of distinct compositions.

The phrase "sequential administration" means that the antimicrobial (or the antimicrobial mixture) and the compound according to the invention (or the compound mixture according to the invention) are administrated not simultaneously but separately in time, one after the other.

The term "to potentiate" an antimicrobial means that the use of a compound according to the invention makes it possible to achieve a prophylactic or therapeutic effect higher than the prophylactic or therapeutic effect achieved using said antimicrobial(s) alone. This can be expressed in different alternative or cumulative manners: increase in the antimicrobial effect, decrease in the antimicrobial dose at a constant antimicrobial effect, reduction in the MIC. Further, potentiation enables the resistance appearance to be reduced, or even cancelled.

The phrase "increasing an antimicrobial effect" means: the widening of a microbial spectrum of the antimicrobial activity, the increase in the antimicrobial action rate, the improvement of the cure rate or of the time to cure rate of the antimicrobial, at a constant antimicrobial dose.

The phrase "decreasing the antimicrobial amount used" means that the use of the compound according to the invention makes it possible to use an antimicrobial amount lower than the antimicrobial amount normally necessary to achieve a given therapeutic or prophylactic effect when the antimicrobial is administrated alone. The decrease in the antimicrobial amount used can be more or less high; it is preferably at least 10%, and more preferably at least 20%, further preferably at least 40%, or even 50% or more with respect to the amount normally necessary to achieve a given therapeutic or prophylactic effect.

"MIC" means "minimum inhibitory concentration", which is the lowest concentration of substance at which a microbial growth is no longer observed after 18 to 24 h of contact under conditions in favour of microbial growth.

Inhibitory minimum concentration measurement tests are made in a solid agar medium according to international standards in force (CLSI M7-A9 Jan 12 standards): dispersion of the compounds to be tested in a Mueller Hinton gelose. An adaptation relating to the hydrophobicity of compounds and compositions is however necessary to disperse them in the medium: dilution of the compounds in a solvent. The compounds and compositions incorporated in the agar medium can be diluted beforehand in one or more solvents (Tween® 80 diluted with water, tween® 80 diluted with propylene, DMSO diluted with water). The strains are deposited onto the agar surface with a steers apparatus. In the examples, different dissolution methods for products are tested in parallel to circumvent the problems of water/solvent distribution coefficient of the molecules (antimicrobial and potentiator) whereas the bacteria grow only in the aqueous phase. The technical requirement will not intervene in in vivo tests. The same dilution methods can be implemented in a liquid medium (microplates and tubes). The same methodology is implemented with fungi.

The MIC 50 and MIC 90 respectively represent concentrations which inhibit 50% and 90% in number of the strains of a same genus.

By "halogen atom", it is intended, for the purposes of the present invention, fluorine, chlorine, bromine and iodine atoms.

By "heteroatom", it is intended, for the purposes of the present invention, N, O or S, advantageously O.

By "($C_1$-$C_6$)alkyl" group, it is intended, for the purposes of the present invention, a saturated, linear or branched, monovalent hydrocarbon chain, comprising 1 to 6, preferably 1 to 4, carbon atoms. By way of examples, methyl, ethyl, propyl, isopropyl, butyl, isobutyl, sec-butyl, tert-butyl, pentyl or even hexyl groups can be mentioned.

By "($C_2$-$C_6$)alkenyl" group, it is intended, for the purposes of the present invention, a linear or branched, monovalent hydrocarbon chain, including at least one double bond and including 2 to 6 carbon atoms. By way of example, ethenyl or allyl groups can be mentioned.

By "($C_1$-$C_6$)haloalkyl", it is intended, for the purposes of the present invention, a ($C_1$-$C_6$)alkyl group, as defined above, for which one or more hydrogen atoms have been replaced with a halogen atom as defined above. It can be in particular a CF3 group.

By "($C_1$-$C_6$)alkoxy" group, it is intended, for the purposes of the present invention, a ($C_1$-$C_6$)alkyl group as defined above, linked to the rest of the molecule through an oxygen atom. By way of example, methoxy, ethoxy, propoxy, isopropoxy, butoxy or even tert-butoxy groups can be mentioned.

By "($C_2$-$C_6$)alkenoxy" group, it is intended, for the purposes of the present invention, a ($C_2$-$C_6$)alkenyl group, as defined above, linked to the rest of the molecule through an oxygen atom. By way of example, the —OCH$_2$CH=CH$_2$ group can be mentioned.

By "($C_1$-$C_6$)alkylene" or "($C_1$-$C_6$)alkanediyl" group, it is intended, for the purposes of the present invention, a linear or branched divalent hydrocarbon chain, comprising 1 to 6 carbon atoms, as for example, a methylene, ethylene, propylene, butylene, pentylene or even hexylene group.

By "($C_2$-$C_6$)alkenylene" or "($C_2$-$C_6$)alkenediyl" group, it is intended, for the purposes of the present invention, a linear or branched divalent hydrocarbon chain, comprising 2 to 6 carbon atoms and at least one double bond, as for example, a vinylene (ethenylene) or propenylene group.

DESCRIPTION OF THE INVENTION

The object of the invention is an antimicrobial agent potentiated by a compound of the formula I for use in treating a microbial infection. Thus, another object of the invention is a combination of an antimicrobial agent and a compound having the following formula I:

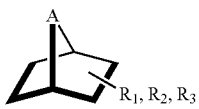

(I)

wherein $R_1$, $R_2$, $R_3$ are each, independently of one another, H, OH, a ($C_1$-$C_6$)alkyl, ($C_2$-$C_6$)alkenyl, ($C_1$-$C_6$)haloalkyl, ($C_1$-$C_6$)alkoxy, ($C_2$-$C_6$)alkenoxy, ($C_1$-$C_6$)haloalkoxy, —O—CO—($C_1$-$C_6$)alkyl group;

A is a heteroatom or a R-(Het)-R' or -(Het)-R group wherein R, R', are each, independently of one another, a ($C_1$-$C_4$) alkanediyl group optionally substituted by $C_1$-$C_4$ alkyl radicals and Het represents a heteroatom, A is advantageously a -(Het)-R group in a compound of formula (I): antimicrobial agent mass ratio, ranging from 8:1 to 1:10, and the antimicrobial agent is not a terpenoid or a phenylpropanoid.

The antimicrobial agent is advantageously an active ingredient of western conventional medicine, as will be described in the following. In particular, the antimicrobial agent is not a terpenoid or a phenylpropanoid, such as an essential oil extract or an essential oil component.

The compound of formula (I): antimicrobial agent mass ratio ranges more particularly from 4:1 to 1:10, more advantageously from 1:1 to 1:10, further advantageously from 1:1 to 1:5.

This means that the administrated dose of the compound of formula (I) is in the same order of magnitude as that of the antimicrobial agent.

The mass ratio corresponds to the dose ratio in mg/kg of the compound and the antimicrobial agent to be administrated to humans or animals.

Surprisingly, it has been noticed that the potentiating effect decreases when the dose of the compound according to the invention (or compound mixture according to the invention) increases. This potentiating effect can reappear at the MIC of the compound alone, but this is not the object of the invention.

Within the scope of the present invention, in vitro, the concentration of the inactive compound, at which a potentiating effect is observed, is very far from the threshold of the antimicrobial properties (MIC), when antimicrobial properties are observed. By very far, it is intended that the in vitro concentration is at least 10 times, advantageously at least 20 times, more advantageously at least 50 times, or further advantageously at least 100 times lower than the MIC.

In particular, on a pathogenic strain A, which induces in particular the microbial infection considered, the concentration of compound (I) advantageously meets the following equation:

$$[C] < [MIC]/x$$

where [C] is the concentration according to the invention of compound (I) to be used on the strain A

[MIC] is the MIC measured for the compound (I), alone, on this strain A x is higher than or equal to 100, advantageously to 1 000, more advantageously x is between 2 000 and 10 000, or even higher than 50 000.

In vitro, the doses of compound (I) are lower than 100 mg/L, advantageously lower than 64 mg/L, more advantageously between 0.01 and 25 mg/L, more advantageously between 1 and 16 mg/L.

In the compositions administrated, the concentration, per unit dose per kilogram, of the compound of formula (I) is advantageously lower than 100 mg, more advantageously lower than 64 mg.

The compounds (I) can be used at a low concentration (in vitro at concentrations in the order of one µg/ml) to potentiate antimicrobials, which is quite compatible with a future use in humans or animals (in particular if a systemic administration is intended).

This makes it possible to contemplate dosing in humans or animals being lower than 64 mg/kg, advantageously between 0.01 and 64 mg/kg, more advantageously between 0.5 and 40 mg/kg, further advantageously between 5 and 30 mg/kg.

The potentiator compound according to the invention is advantageously administrated at a concentration such that its maximum serum concentration is lower than 250 mg/L, advantageously lower than 150 mg/L, more advantageously between 10 and 150 mg/L after administration.

Of course, at these concentrations, the compound can be administered to humans and animals, including systemically, and has no major adverse effects, in particular carcinogenicity or genotoxicity.

The compound according to the invention (or compound mixture according to the invention): antimicrobial mass ratio depends each time on the antimicrobial used and it will be adapted to each case.

For example, for amoxicillin in the cases where it is usually administrated at a 1 000 mg dose per administration, the dose of the compound of formula (I) could range between 300 and 850 mg per administration, or less. However, for colistine which is usually administrated at a 1 MUI dose by the pulmonary route, the dose of the compound of formula (I) could range between 0.1 and 0.8 MUI, or even less.

Otherwise stated, one object of the invention is a process for potentiating the antimicrobial activity of an antimicrobial independently of the resistance mechanism comprising the following steps of:
  a) choosing a compound of formula (I) which is therapeutically inactive (for anti-infectious purposes) alone at the contemplated dose,
  b) preparing a composition comprising the compound chosen in step a) with the antimicrobial.

Another object of the invention is also a method for treating and/or preventing a microbial infection in a subject, comprising co-administrating in the subject having said microbial infection an antimicrobial and a compound of formula (I).

The compound and antimicrobial are adapted for a simultaneous, separated or spread over time administration to humans or animals.

The antimicrobial is preferably an antibiotic. It can also be an antifungal.

Surprisingly, it has been noticed that the compounds of formula (I), used at this low concentration, are capable of potentiating the activity of antimicrobials. Thus, the use of these potentiators advantageously enables said antimicrobial to be used at a lower concentration and/or at a usual concentration while having a higher activity than the antimicrobial alone at the same dose (increase in the effect intensity or the effect kinetics).

Concretely, the invention makes it possible in particular:

A/to decrease the doses at a constant effect: decrease in the necessary amount of an antimicrobial for inhibiting/destroying usually sensitive microbes, B/to increase the effect at a constant dose: increase in the capacity of an antimicrobial to inhibit/destroy sensitive germs (improvement in the effect kinetics, in the effect intensity, and widening of the activity spectrum of an antimicrobial to germs which were inconstantly sensitive or resistant to the antimicrobial).

Reducing the administrated dose (A/) of an antimicrobial has an interest not only from the treatment point of view for microbial infections in humans or animals in particular reduction of side effects, but also, being not negligible, for an environment point of view (decrease in the onset of antimicrobial resistances). The use of known antimicrobials at lower doses can aid in fighting against the onset of new resistance mechanisms. In particular, the antimicrobial can be used at a reduced dose, at which the administrated dose of antimicrobial corresponds from $1/50$ to $3/4$ of the necessary dose of antimicrobial in the absence of co-administration of a compound according to the invention for an administration to a subject (man, animal) to treat microbial infections. The decrease in the antimicrobial dose at a constant effect enables the toxicity of said antimicrobial to be limited. In application to commercial animals, this enables latency times to be reduced before slaughtering.

The dose reduction also makes it possible to contemplate reusing some antimicrobials, which to date cannot be administrated any longer because they have at their efficient doses side effects which are important, and can again be administrated efficiently in humans or animals with few side effects.

Increasing the effect of an antimicrobial at a constant dose (B/) has a certain clinical interest both from the quantitative point of view by improving the kinetics of an antimicrobial effect and from a qualitative point of view by making it possible to treat a patient (human or animal) having a microbial infection with an antimicrobial for which the strain was sensitive or inconsistently sensitive in the absence of potentiation. The increase in the antimicrobial effect rate enables the time spent in the "infecting" condition by the patient or animal to be decreased, thus reducing the disease epidemiology as well as the occurrence and diffusion of resistances.

By virtue of the presence of the compounds according to the invention, it is possible to increase the bactericidal rate of the antimicrobial at a constant antimicrobial dose. Thus, the action rate of a potentiated antimicrobial can be increased. This is particularly true for concentration-dependent antimicrobials.

By virtue of the presence of the compounds according to the invention, the spectrum of the antimicrobial can be widened, in particular at a constant antimicrobial dose. Thus, an antimicrobial potentiated by the compounds according to the invention can be used on strains on which it is no longer sensitive in the absence of potentiation (in particular because of the onset of resistances).

In one embodiment, the compound of the formula (I) is sufficient to potentiate the antimicrobial, with the consequence that the use of a single compound of formula (I) is sufficient to potentiate the antimicrobial. However, in some cases, a combination use of inactive compounds can be contemplated. This is particularly true when a wide spectrum activity is intended. In particular, to potentiate an antibiotic on Gram+ and Gram− bacteria, it can be useful to co-administrate a compound according to the invention being particularly potentiator on Gram+ bacteria and a compound according to the invention being particularly potentiator on Gram− bacteria.

In formula (I) $R_2$ and $R_3$ are each H, $R_1$ is a $(C_1$-$C_6)$alkyl group, and A is the heteroatom O or an R—O—R' or —O—R' group, where R, R' are each, independently of one another, a $(C_1$-$C_2)$alkanediyl group optionally substituted with $C_1$-$C_4$ alkyl radicals.

Advantageously, the compound of formula (I) is cineol.

Within the scope of the present invention, the microbial infection is advantageously an infection induced by a pathogen chosen from the following potentially pathogenic genera: *Acetobacter, Acetobacterium, Acinetobacter, Citrobacter, Enterobacter, Enterococcus, Escherichia, Helicobacter, Klebsiella, Proteus, Providencia, Pseudomonas, Salmonella, Serratia, Staphylococcus, Streptococcus, Actinobacillus, Neisseria, Mannheima, Pasteurella, Candida, Aspergillus, Cryptococcus, Trichosporon, Malassezia,* and *Mycobacterium.*

The bacterial strain or species is advantageously chosen from the group consisting of: *Acetobacter, Acetobacterium, Acinetobacter, Actinobacillus, Citrobacter, Enterobacter, Enterococcus, Escherichia, Helicobacter, Klebsiella, Mannheima, Pasteurella, Proteus, Providencia, Pseudomonas,*

*Salmonella, Serratia, Staphylococcus,* and *Streptococcus.* More particularly, the bacterial strain or species is advantageously chosen from the group consisting of *Citrobacter freundii, Enterobacter aerogenes, Enterobacter cloacae, Escherichia coli, Klebsiella oxytoca, Klebsiella pneumoniae, Proteus mirabilis, Providencia stuartii, Salmonella* sp, *Serratia marcescens, Acinetobacter baumannii, Burkholderia cepacia, Pseudomonas aeruginosa, Staphylococcaceae, Staphylococcus aureus, Enterococcus faecium,* and *Enterococcus* sp. Thus, the bacterium can indifferently be a gram- bacterium or a gram+ bacterium.

The bacterium is more advantageously chosen from the group consisting of *Pseudomonas aeruginosa, Escherichia coli, Enterococcus faecalis, Klebsiella pneumoniae* and *Staphylococcus aureus.*

The fungus is advantageously chosen from the group consisting of: *Candida, Aspergillus, Cryptococcus Trichosporus.* The fungus is more advantageously *Candida albicans.*

The mycobacterium is advantageously *Mycobacterium tuberculosis.*

The antimicrobial agent can be an antibiotic and/or an antifungal agent. In a preferred alternative, the compound of formula (I) and the antimicrobial do not belong to the same family of chemical compounds. Thus, since the compound of the formula (I) is a terpenoid derivative, the antimicrobial is not a terpenoid, or even is not an essential oil extract or a phenylpropanoid.

The antibiotics which can be used in the present invention are advantageously chosen from:
1. antibiotics active on membranes, in particular beta-lactamins, penicillins, cephalosporins, glycopeptides, phosphomycins, polymixins, bacitracin, cycloserine;
2. protein synthesis inhibiting antibiotics, in particular aminosides, teracyclines, fusidic acid, chloramphenicol and derivatives thereof, macrolides, lincosamides, streptogramins, synergistins and oxazolidinones;
3. nucleic acid synthesis inhibiting antibiotics, in particular quinolones, nitrofurans, ansamycins and fucidic acid;
4. folate synthesis inhibiting antibiotics, in particular sulphamides and sulphamide combinations;
5. mycolic acid synthesis inhibiting antibiotics, in particular isoniazid, prothionamid, ethionamide, pyrazinamide;
6. any of their pharmaceutically acceptable salts, and
7. any of their combinations.

Preferably, the antibiotic is chosen from: peptidoglycan synthesis inhibiting antibiotics, nucleic acid synthesis inhibiting antibiotics, folate synthesis inhibiting antibiotics, mycolic acid synthesis inhibiting antibiotics, any of their pharmaceutically acceptable salts, and any of their combinations. The particularly advantageous antibiotic class is that of the peptidoglycan synthesis inhibiting antibiotics.

In particular, the antibiotic is chosen from: amoxicillin, amoxicillin/clavulanic acid, imipenem, vancomycin, erythromycin, azithromycin, gentamicin, amikacin, colistin, clindamycin, ciprofloxacin, tigecycline.

In an alternative of the invention, the microbial infection is a bacterial infection induced by a bacterial strain, of the cocci or positive-gram bacillus type, and the antimicrobial is amoxicillin.

In one alternative of the invention, the amoxicillin is dosed at 1 000 mg/administration and cineol is dosed at 1 000 mg/administration, advantageously 500 mg/administration more preferentially to 250 mg/administration.

In another alternative of the invention, the microbial infection is a bacterial infection induced by a methicillin-resistant *E. coli* or *S. aureus* type bacterial strain and the antimicrobial is an amoxicillin/clavulanic acid mixture.

In another alternative of the invention the amoxicillin/clavulanic acid mixture: cineol ratio is 10:1, 1:1 or even 1:5.

In another alternative of the invention, the microbial infection is a bacterial infection induced by an enterobacteria type strain *Pseudomonas* or *S. aureus,* and the antimicrobial is ciprofloxacin.

Antifungals which can be used in the present invention are advantageously chosen from:
1. antifungals acting on the membrane, in particular polyenes, azoles, allylamines and thiocarbamates, echinocandins
2. antifungals acting on nucleic acid synthesis, in particular griseofulvin, fluorocytosine
3. antifungals acting on microtubules, in particular griseofulvin.

The antifungal is advantageously chosen from polyenes, azoles, allylamines, thiocarbamates, echinocandins, griseofulvin, and fluorocytosine.

In another alternative of the invention, the microbial infection is a vaginal mycosis and the antibiotic is sertaconozole.

The compounds according to the invention are advantageously systemically administrated. Thereby, they are adapted for systemic administration.

The compounds according to the invention can be used in any pharmaceutical composition formulated so as to facilitate administration thereof. The pharmaceutical composition can comprise all the pharmaceutically acceptable excipients which are usually used such as vehicle(s) or diluent(s).

The pharmaceutical composition can be administrated by the oral, enteral, parenteral (intravenous, intramuscular or sub-cutaneous, intraperitoneal), transcutaneous (or transdermal or percutaneous), cutaneous, mucosal, (in particular transmucosal-buccal, nasal, ophthalmic, otologic, vaginal, rectal) route, or even the intragastric, intracardial, intraperitoneal, intrapulmonary or intratracheal routes.

The pharmaceutical composition can be in dry form, which dry form is to be reconstituted at the time of the use (powder, lyophilisate, etc.), in solid form (in particular cachet, powder, capsule, pill, granule, suppository, tablet, and more precisely accelerated release tablet, enteric-coated tablet or sustained release tablet), in pasty form (in particular gel, ointment, cream or ovule), in liquid form (in particular syrup, injectable, infusible or drinkable (elixir) solution or collyrium), in the form of an aerosol (spray, vapour or gas), in the form of a patch, in an injectable form (is an aqueous, non-aqueous or isotonic solution).

On the other hand, the pharmaceutical composition can be packaged for an administration in the form of a single (single dose) or multiple (multidose) dose.

The antimicrobial(s) and the compound(s) according to the invention can be administrated in a same pharmaceutical composition or in distinct pharmaceutical compositions, simultaneously, sequentially or spread over time. In case of separated administration, the forms of the pharmaceutical compositions can be similar or distinct; the administration routes can be identical or distinct.

The administration schedule will be adapted by the clinician depending on the case. The administration routes and the dosages vary as a function of a variety of parameters, for example as a function of the patient condition, the infection type and the severity of the infection to be treated or the antimicrobial used.

The animal is preferably a mammal, in particular humans, pets, or commercial animals.

The examples that follow illustrate the invention.

MIC measurement: the minimum inhibitory concentration measurement tests are made in an agar solid medium according to international standards in force (CLSI standards), according to the previously defined protocol. The compounds and compositions incorporated in the agar medium can be diluted beforehand in one or more solvents (Tween® 80 diluted with water—3.4 ml Tween for 9.6 ml water—, tween® 80 diluted with propylene 10-3.4 ml Tween for 9.6 ml propylene—, or DMSO diluted with water).

The booster contribution as compared with the MIC of the antibiotic alone is expressed in a (MIC ATB)/(MIC ATB+booster) ratio. Thereby, gains are defined:

MIC 50 gain=(MIC50 of the antibiotic alone)/(MIC50 (antibiotic+booster))

MIC 90 gain=(MIC90 of the antibiotic alone)/(MIC90 (antibiotic+booster))

The booster is a generic term to designate the potentiator compounds of the invention, of formula (I).

Unless otherwise indicated, the ratios indicated in the tables are mass ratios.

Mass Ratios Used

- 64/500 corresponds to about 1 to 8 (noted 1 to 8 in the tables)
- 64/100 corresponds to about 1 to 1,5 (noted 1 to 1.5 in the tables)
- 64/50 corresponds to about 1 to 0.75 (noted 1 to 0.75 in the tables)
- 64/10 corresponds to about 1 to 0.15 (noted 1 to 0.15 in the tables)

Description of the Test Protocols/Test Strains.

Bacterial Strains

The tested strains are isolated from various human samples (blood, urine, pulmonary aspirates, etc.). The strains investigated in the following examples are chosen from the strains of the following table:

TABLE 2

| Enterobacteriaceae, n = 11 | |
|---|---|
| Escherichia coli | Phenotypic characterisation: BLSE, wild, penicillinase, fluoroquinolone resistance, nalixidic acid resistance. Other gram bacilli, n = 10 |
| Pseudomonas aeruginosa | Genotypic characterisation: BLSE, cephalosporinase, penicillinase, absence of porine, multiresistance, wild Staphylococcaceae, n = 10 |
| Staphylococcus | Phenotypic characterisation: methicillin-, fluoroquinolone-, kanamycin-, tobramicin-resistance, multiresistance, wild Streptococcus and app, n = 2 |
| Enterococcus sp | Phenotypic characterisation: erythromycin-, clindamycin-, pristinamicin-resistance, wild |

The yeast strains tested (n=33) belong to the Candidas albicans, Candida tropicalis, Candida krusei, Candida parapsilosis, Candida glabrata species.

EXAMPLE 1

Minimum Inhibitory Concentration Measurement

Mic of Cineol Alone (Any Solvents)

TABLE 3

| | | Cineol | | | |
|---|---|---|---|---|---|
| | | water/water | Tween/water | Tween/prop glyc | DMSO |
| Pyo | MIC 50 | >1 | >1 | >1 | 1 |
| | MIC 90 | >1 | >1 | >1 | 1 |
| Coli | MIC 50 | >1 | >1 | >1 | >1 |
| | MIC 90 | >1 | >1 | >1 | >1 |
| Staph | MIC 50 | >1 | >1 | >1 | >1 |
| | MIC 90 | >1 | >1 | >1 | >1 |

The products are tested in successive dilutions from 1% to 0.00375%. The value >1% indicates that no bacterial inhibition has been observed at the concentrations tested. A value equal to 1.00% corresponds to 10 000 mg/L (that is 10 g/L).

1/Aerobic vs Anaerobic Test in DMSO and Tween® 80

The potentiating effect of Augmentin® with cineol has been tested on different strains under aerobic/anaerobic conditions. The Augmenting/cineol mass ratio is 64 to 100 (1 to 1.5). The MICs are measured on different strains. Then, the MIC gain is calculated on the strains belonging to the same genus.

The MIC gain expresses the following ratio: MIC (50 or 90) with potentiator/MIC (50 or 90) without potentiator. The results are reported in the following table:

TABLE 4

| | | aerobic | | anaerobic | |
|---|---|---|---|---|---|
| | | Tween® 80 | DMSO | Tween® 80 | DMSO |
| E. Coli | MIC 50 Gain | 0.75 | 1.00 | 0.67 | 0.67 |
| | MIC 90 Gain | 1.00 | 0.77 | 0.37 | 0.37 |
| Staphylococcus | MIC 50 Gain | 0.50 | 0.50 | 0.50 | 0.50 |
| | MIC 90 Gain | 1.00 | 1.00 | 0.55 | 0.60 |

This test shows that cineol enables the Augmentin® effect to be potentiated on large series of strains. The potentiating effect is expressed under aerobic or anaerobic conditions and can be influenced by the solvent involved for dispersing products.

2/Aerobic Test with Direct Dilution in Water

The same measurements and calculations are made in water, with Augmentin® or amoxicillin alone.

The results are reported in the following table:

TABLE 5

| | | Augmentin®/cineol 1:1.5 | Augmentin®/cineol 1:0.75 | amoxicillin/cineol 1:1.5 |
|---|---|---|---|---|
| E. Coli | MIC 50 Gain | 1.33 | 1.33 | 1.00 |
| Staphylococcus | MIC 130 Gain | 0.50 | 0.75 | 0.83 |
| | MIC 170 Gain | 0.55 | 0.50 | 1.00 |

This test shows that cineol tested in vitro in another solvent shows slightly different potentiating effects. Here, the synergy is no longer apparent on *E. coli* with a direct dilution with water whereas it is clearly visible in another solvent (Ex 1-1). Thus, a neutral result in a solvent does not suggest a neutral result in another solvent.

This test also shows that the effect is ratio-dependent.

3/Amoxicillin (AMX) and Augmentin® (AUG) Tests in Tween®80/Water vs DMSO

The mass ratios are the following ones.
The results are reported in the following table:

TABLE 6

| | | AMX/ Cineol 1:8 Tween water | AMX/ Cineol 1:8 DMSO | AMX/ Cineol 1:1.5 Tween water | AMX/ Cineol 1:1.5 DMSO | AMX/ Cineol 1:0.15 Tween water | AMX/ Cineol 1:0.5 DMSO |
|---|---|---|---|---|---|---|---|
| *E. Coli* | MIC 50 Gain | 2.00 | 1.33 | 2.00 | 1.33 | 2.00 | 2.00 |
| *Staphylococcus* | MIC 50 Gain | 0.75 | 1.33 | 0.38 | 1.33 | 1.00 | 1.50 |
| | MIC 90 Gain | 0.50 | 1.00 | 1.00 | 1.00 | 0.50 | 1.00 |

Once again, potentiations seem to disappear depending on the bacterial type and depending on the solvent. The tween associated with water enables potentiation of amoxicillin by cineol to be clearly highlighted.

The results are reported in the following table:

TABLE 7

| | | Aug/Cineol 1:8 | | Aug/Cineol 1:1.5 | | Aug/Cineol 1:0.15 | |
|---|---|---|---|---|---|---|---|
| | | Tween water | DMSO | Tween water | DMSO | Tween water | DMSO |
| *Coli* | MIC 50 Gain | 1.00 | 2.00 | 0.75 | 2.00 | 1.00 | 2.00 |
| | MIC 90 Gain | 0.77 | 2.00 | 1.00 | 1.00 | 0.77 | 1.30 |
| *Staph.* | MIC 50 Gain | 1.00 | 1.00 | 0.50 | 0.50 | 1.00 | 1.00 |
| | MIC 90 Gain | 1.00 | 1.00 | 1.00 | 1.00 | 1.00 | 2.00 |

The dilution of Augmentin® with water and tween enables the potentiating effect to be highlighted at low doses (up to 0.025 mg/l cineol) since the MIC of Augmentin® alone on these strains can be 0.25 mg/l on some staphylococci.

4/CIP (Ciprofloxacin) Tests in Tween®80/Water, vs DMSO

The results are reported in the following table:

TABLE 8

| | | CIP/Cineol 1:8 | | CIP/Cineol 1:1.5 | | CIPCineol 1:0.015 | |
|---|---|---|---|---|---|---|---|
| | | Tween water | DMSO | Tween water | DMSO | Tween water | DMSO |
| *Pyo.* | MIC 90 Gain | 0.91 | 0.55 | 1.82 | 0.50 | 1.00 | 0.50 |
| *Coli* | MIC 90 Gain | 0.53 | 0.30 | 0.53 | 0.27 | 0.60 | 0.27 |

TABLE 8-continued

| | | CIP/Cineol 1:8 | | CIP/Cineol 1:1.5 | | CIPCineol 1:0.015 | |
|---|---|---|---|---|---|---|---|
| | | Tween water | DMSO | Tween water | DMSO | Tween water | DMSO |
| *Staph* | MIC 90 Gain | 1.00 | 0.19 | 1.16 | 1.43 | 1.16 | 1.43 |

The test shows that cineol also potentiates ciprofloxacin at low cineol doses (synergies are observed at 0.125 mg cineol doses). The solvent and ratio have both an influence on the result.

5/Tetracycline (TE) Tests in Water, Tween, TE, T/P

The results are reported in the following table:

TABLE 9

| | | TE/Cineol 1:1.5 Tween water | TE/Cineol 1:1.5 Tween Propylene Glycol | TE/Cineol 1:1.5 DMSO | TE/Cineol 1:1.5 water |
|---|---|---|---|---|---|
| *Pyo* | MIC 50 Gain | 0.50 | 2.00 | 0.67 | 1.50 |
| | MIC 90 Gain | 1.00 | 1.00 | 0.50 | 1.00 |
| *Coli* | MIC 50 Gain | 1.00 | 2.00 | 1.00 | 1.00 |
| | MIC 90 Gain | 0.50 | 1.20 | 1.00 | 1.00 |
| *Staph* | MIC 50 Gain | 1.00 | 1.00 | 1.00 | 1.00 |
| | MIC 90 Gain | 0.91 | 1.00 | 0.91 | 1.00 |

The test shows the capacity of cineol to potentiate tetracycline, in particular in DMSO and the Tween-water mixture.

6/GEN (Gentamycin) Tests in WATER/Tween®80+Water/Tween®80+Propylene Glycol

The results are reported in the following table:

TABLE 10

|  | | water | | Tween | | Tween dilution prop glycol | |
|---|---|---|---|---|---|---|---|
|  | | GEN/ Cineol 1:8 | GEN/ Cineol 1:1.5 | GEN/ Cineol 1:8 | GEN/ Cineol 1:1.5 | GEN/ Cineol 1:8 | GEN/ Cineol 1:1.5 |
| Pyo | MIC 50 Gain | 1.00 | 1.00 | 1.00 | 1.00 | 2.00 | 2.00 |
|  | MIC 90 Gain | 1.00 | 1.11 | 1.00 | 0.90 | 3.98 | 1.00 |
| Coli | MIC 50 Gain | 1.00 | 2.00 | 1.00 | 1.00 | 2.00 | 0.50 |
|  | MIC 90 Gain | 1.00 | 1.00 | 1.00 | 0.55 | 2.00 | 0.50 |
| Staph | MIC 50 Gain | 1.00 | 2.00 | 1.00 | 1.00 | 1.00 | 0.50 |
|  | MIC 90 Gain | 1.00 | 1.25 | 1.50 | 1.50 | 2.00 | 0.83 |

The test demonstrates the capacity of cineol to potentiate gentamycin, in particular in the tween+propylene mixture.

7/Sertaconazole in DMSO

The potentiating effect of cineol on yeasts (*candida albicans*) is also tested. The results are reported in the following table:

TABLE 11

| Sertaconazole + cineol 1:1.5-DMSO | |
|---|---|
| MIC 90 Gain | 0.5 |
| MIC 50 Gain | 0.25 |

This test demonstrates that cineol is able to potentiate sertaconazole.

EXAMPLE 2

Double Dilution Test

The double dilution test is a MIC measurement test made on successive dilutions of the 2 products of the composition. Thus, 12 dilutions of the booster (cineol) are tested with 12 dilutions of the antibiotic (Amoxicillin). The summary table expresses for each strain and for each dilution of the booster the measured antibiotic MIC.

It is noticed that cineol is capable of potentiating (additive phenomena) amoxicillin at very high concentrations (MIC 50 000 mg/L). When the concentration of cineol decreases, there is no potentiating phenomena any longer. Surprisingly, this potentiation reappears when the cineol dose is very low.

Tests have also been made with Augmentin® (amoxycillin/clavulanic acid) where the same results are observed. An isobologram revealing the amoxicillin MIC curve observed as a function of concentration (dilution) of cineol (strain: SA8238) is reported in FIG. 1. A synergy is noticed at high and low cineol doses, with an unexpected discontinuity.

EXAMPLE 3 etest

The corresponding tests are made based on the usual MIC test: the etest® (Biomerieux) strip is deposited onto the surface of a seeded agar medium in which the booster has been incorporated. This test enables solvent effect risks, that is a possible interaction with the solvent used in vitro, to be minimised.

The MIC of the antibiotic alone (Tween water control or DMSO control), or in association with cineol at three different concentrations (1 mg/L, 4 mg/L, 16 mg/L) in different solvents (Tween®80 or DMSO) is measured.

The control corresponds to the test made without cineol. A control is made in each solvent tested: distilled water, Tween/water and DMSO.

TABLE 12

| | | in MIC of cineol (in mg/L) | | | | | | | | | | | | | |
|---|---|---|---|---|---|---|---|---|---|---|---|---|---|---|---|
| Name | Reference | 50,000 5 | 25,000 2.5 | 10,000 1 | 5,000 0.5 | 2,500 0.25 | 1,250 0.125 | 600 0.06 | 300 0.03 | 150 0.015 | 75 0.0075 | 37.5 0.00375 | 20 0.002 | 10 0.001 | Amox 0 | Cineol alone |
| E. coli | ATCC 25922 | 0.06+ | 4+ | * | 8 | 16 | 8 | 8 | 8 | 8 | 8 | 8 | 8 | 0.5+ | 8 | >2.5 |
|  | 8137 | 0.25+ | 4+ | * | 8 | 8 | 8 | 8 | 8 | 8 | 8 | 8 | 8 | 0.5+ | 8 | >2.5 |
|  | 8151 | 0.25+ | 4+ | 4+ | 8 | 8 | 8 | 8 | 8 | 8 | 8 | 8 | 8 | 0.5+ | 8 | >2.5 |
|  | 8155 | 0.25+ | 4 | 8 | 8 | 8 | 8 | 8 | 8 | 8 | 8 | 8 | 8 | 0.5+ | 8 | >2.5 |
|  | 8156 | 4+ | 8 | 8 | 8 | 16 | 8 | 8 | 8 | 8 | 8 | 8 | 8 | 0.5+ | 8 | >2.5 |
| Staphylococcus | 8148 | 0.25+ | 16 | 4 | 8 | 8 | 8 | 8 | 8 | 8 | 8 | 8 | 8 | 0.5+ | 8 | >2.5 |

The code enabling the results to be interpreted is the following one: no sign "+" if the MIC is equivalent with and without booster, a sign "+" if the value is lower with booster.

ED control=antibiotic alone in distilled water
DMSO control=antibiotic alone in DMSO
TE control=antibiotic alone in Tween® 80

On these strains, cineol, used alone, has a MIC50 higher than 10 000 mg/L.

In the tables, the colour code enabling the results to be interpreted is the following one: no colour if the MIC is equivalent with and without booster, grey if the value is lower with booster.

TABLE 13

| MIC in mg/L | Coli 8150 | | | Coli 8138 (penicillinase) | | | MRSA 10178 | | |
|---|---|---|---|---|---|---|---|---|---|
| | Tigecycline | Pipera tazo | Meropenem | Cefoxitin | Pipera tazo | Cefoxitine | Tigecycline | Clindamycin | Penicillin G |
| ED control | 0.125 | 0.75 | 0.047 | 3 | 6 | 6 | 0.125 | 0.094 | 1 |
| Tween water control | 0.125 | 1 | 0.094 | 6 | 6 | 6 | 0.125 | 0.19 | 0.5 |
| DMSO control | 0.19 | 1.5 | 0.094 | 8 | 16 | 6 | 0.25 | 0.064 | 1.5 |
| Cineol 1 mg Tween/water | 0.125 | 1.5 | 0.064$^+$ | 3$^+$ | 3$^+$ | 4$^+$ | 0.125 | 0.064$^+$ | 0.5 |
| Cineol 1 mg DMSO | 0.19 | 1$^+$ | 0.064$^+$ | 8 | 6$^+$ | 4$^+$ | 0.19$^+$ | 0.094 | 0.75$^+$ |
| Cineol 4 mg Tween/water | 0.094$^+$ | 0.75$^+$ | 0.047$^+$ | 3$^+$ | 6 | 3$^+$ | 0.094$^+$ | 0.064$^+$ | 0.38$^+$ |
| Cineol 4 mg DMSO | 0.125$^+$ | 1$^+$ | 0.064$^+$ | 3$^+$ | 8$^+$ | 4$^+$ | 0.19$^+$ | 0.064 | 0.5$^+$ |
| Cineol 16 mg Tween/water | 0.1$^+$ | 0.1$^+$ | 0.1 | 1$^+$ | 2$^+$ | 1$^+$ | 0.094$^+$ | 0.047$^+$ | 0.125$^+$ |
| Cineol 16 mg DMSO | 0.064$^+$ | 0.75$^+$ | 0.064$^+$ | 3$^+$ | 6$^+$ | 4$^+$ | 0.125$^+$ | 0.047$^+$ | 0.19$^+$ |

Other e-tests are also made in DMSO with amoxicillin in the presence or absence of cineol (absence of cineol=control). The tests are reported in the following table:

TABLE 14

| | | ED control Amox | Cineol 16 mg/L Amox | Cineol 4 mg/L Amox |
|---|---|---|---|---|
| E. coli | ATCC25922 | 16$^+$ | 12$^+$ | 12$^+$ |
| | 8141 | 8$^+$ | 0.1$^+$ | 6$^+$ |
| | 8150 | 8$^+$ | 0.1$^+$ | 6$^+$ |
| | 8156 | 12$^+$ | 8$^+$ | 8$^+$ |
| Staphylococcus | 8143 | 2$^+$ | 1.5$^+$ | 1.5$^+$ |
| | 8146 | 0.5$^+$ | 0.19$^+$ | 0.38$^+$ |
| | 8149 | 1$^+$ | 0.38$^+$ | 0.5$^+$ |
| | 8240 | 24$^+$ | 16$^+$ | 12$^+$ |
| | 8241 | 32$^+$ | 12$^+$ | 8$^+$ |
| | 10168 | 2$^+$ | 1$^+$ | 1$^+$ |

A potentiation is observed on all the strains.

Other e-tests are also made with amoxicillin/clavulanic acid (Augmentin®) in the presence or absence of cineol (control: no cineol, CIN16: 16 mg/L cineol, CIN4: 4 mg/L cineol) DMSO. The tests are reported in the following table:

TABLE 15

| | | ED Control | CIN16 | CIN4 |
|---|---|---|---|---|
| E. coli | ATCC25922 | 12 | 6$^+$ | 8$^+$ |
| Staphylococcus | 8141 | 6 | 0.1$^+$ | 4$^+$ |
| | 8146 | 0.38 | 0.19$^+$ | 0.25$^+$ |
| | 8149 | 0.75 | 0.38$^+$ | 0.5$^+$ |
| | 8238 | 1 | 0.75$^+$ | 0.38$^+$ |
| | 8239 | 6 | 6 | 3$^+$ |
| | 8240 | 4 | 3$^+$ | 3$^+$ |
| | 8241 | 12 | 12 | 8$^+$ |
| | 10168 | 0.75 | 0.5$^+$ | 0.38$^+$ |

Other e-tests are also made on Pasteurella. The results are reported in the following tables:

TABLE 16

| | 14012 | | | | |
|---|---|---|---|---|---|
| | Amox | Augmentin | ciprofloxacin | meropenem | cefoxitin |
| ED control | 0.032 | 0.094 | 0.004 | 0.008 | 0.5 |
| DMSO control | 0.094 | 0.094 | 0.006 | 0.008 | 0.5 |
| TE control | 0.19 | 0.19 | 0.006 | 0.023 | 0.75 |
| 5 mg cineol water | 0.094 | 0.094 | 0.003 | 0.006 | 0.5 |
| 5 mg cineol DMSO | 0.094 | 0.094 | 0.004 | 0.006 | 0.5 |
| 5 mg cineol TE | 0.094 | 0.094 | 0.004 | 0.008 | 0.5 |
| 10 mg cineol water | 0.094 | 0.125 | 0.004 | 0.008 | 0.5 |
| 10 mg cineol DMSO | 0.125 | 0.125 | 0.004 | 0.006 | 0.38 |
| 10 mg cineol TE | 0.094 | 0.125 | 0.006 | 0.008 | 0.5 |

TABLE 17

| | 14013 | | |
|---|---|---|---|
| | Amox | Augmentin | ciprofloxacin |
| ED control | 0.19 | 0.19 | 0.012 |
| DMSO control | 0.19 | 0.25 | 0.012 |
| TE control | 0.25 | 0.25 | 0.016 |
| 5 mg cineol water | 0.25 | 0.25 | 0.012 |
| 5 mg cineol DMSO | 0.25 | 0.19 | 0.012 |
| 5 mg cineol TE | 0.25 | 0.25 | 0.012 |
| 10 mg cineol water | 0.19 | 0.19 | 0.016 |
| 10 mg cineol DMSO | 0.25 | 0.19 | 0.012 |
| 10 mg cineol TE | 0.125 | 0.19 | 0.012 |

TABLE 18

| | 14014 | | |
|---|---|---|---|
| ED control | Amox | meropenem | cefoxitin |
| DMSO control | 0.125 | 0.016 | 0.38 |
| TE control | 0.094 | 0.012 | 0.5 |
| 5 mg cineol water | 0.19 | 0.016 | 0.5 |
| 5 mg cineol DMSO | 0.094 | 0.012 | 0.19 |
| 5 mg cineol TE | 0.094 | 0.016 | 0.38 |
| 10 mg cineol water | 0.125 | 0.016 | 0.38 |
| 10 mg cineol DMSO | 0.125 | 0.016 | 0.5 |
| 10 mg cineol TE | 0.094 | 0.012 | 0.38 |
| ED Control | 0.094 | 0.012 | 0.38 |

EXAMPLE 4

Growth Test/Bactericidal Test

1 Growth test on the strain 10168

The growth tests are made in a liquid medium with a prior dispersing of the booster of the antibiotics in a suitable solvent.

The growth kinetics of bacteria is measured in the presence of Augmentin®, cineol boosted Augmentin® or cineol.

Figure 2:
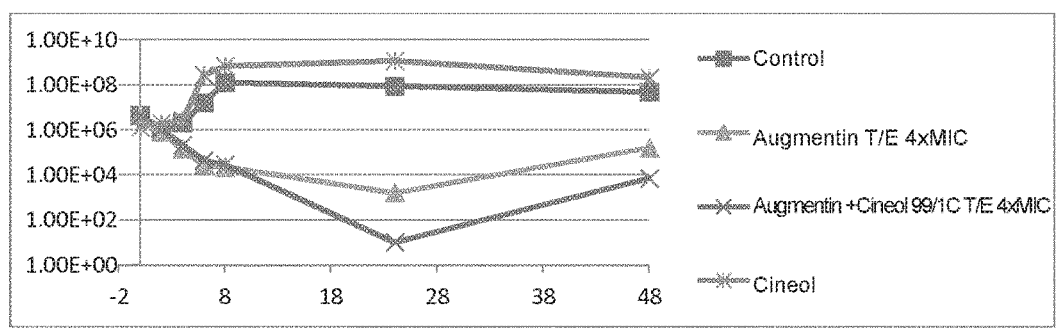
FIG. 2 presents the results of the growth test (strain 10168, genus *Staphylococcus*) of Example 4.

The results are reported in FIG. 2 (strain 10168, genus *Staphylococcus*), the caption of which is:

Square: control (bacterium alone)

Triangle: Augmentin® diluted with a Tween®80/water mixture at a concentration 4 times its MIC Cross (x): Augmentin® and cineol, diluted with a Tween®80/water mixture, Augmentin® is at a concentration 4 times its MIC, Augmentin®/cineol mass ratio 64/100

Star (*): cineol alone diluted with a Tween®80/water mixture.

It is noticed that the presence of cineol, at a very low dose, enables the bactericidal rate of Augmentin® to be accelerated.

2 Post Antibiotic Effect on the Strain 08150 (MIC of Augmentin®=4 mg/L)

The number of bacteria is counted after 16 h contact in the presence of Augmentin® (AC) and/or cineol, and then several hours after the contacting end. Augmentin® is used at its MIC. The results are reported in the following table:

TABLE 19

| | contact time of Augmentin ® + cineol 16 h | | | | | |
|---|---|---|---|---|---|---|
| Time (h) | control | AC MIC | AC MIC Cineol 16 mg/L | AC MIC Cineol 4 mg/L | Cineol 16 mg/L | Cineol 4 mg/L |
| 0 | 2.47E+07 | 2.53E+05 | 1.40E+04 | 1.00E+02 | 2.20E+07 | 2.17E+07 |
| 1 | 9.20E+06 | 3.40E+04 | 7.80E+03 | 9.00E+03 | 3.88E+07 | 4.92E+07 |
| 2 | 7.10E+07 | 1.60E+05 | 5.10E+04 | 3.00E+03 | 6.40E+07 | 5.50E+07 |
| 3 | 2.07E+08 | 1.84E+06 | 7.60E+05 | 3.60E+04 | 2.70E+08 | 3.90E+08 |
| 4 | 3.10E+08 | 9.90E+06 | 6.40E+06 | 3.40E+05 | 4.20E+08 | 3.50E+08 |
| 5 | 6.60E+08 | 3.70E+07 | 3.55E+07 | 2.37E+06 | 5.50E+08 | 5.90E+08 |
| 6 | 4.10E+08 | 2.10E+08 | 2.00E+08 | 1.27E+07 | 5.90E+08 | 6.00E+08 |

Control=absence of cineol and Augmentin®.

It is noticed that the addition of cineol enables the number of bacteria to be significantly reduced, including after contacting.

3 Post Antibiotic Effect on the Strain 08152 (MIC of Augmentin®=0.5 mg/L)

The number of bacteria is counted after 16 h contact in the presence of Augmentin® (AC) and/or cineol, and then several hours after the contacting end. Augmentin® is used at a concentration 4 times its MIC. 4XMIC means that the concentration of antibiotic is 4 times higher than its MIC, measured when it is used alone on the considered strain. The results are reported in the following table:

TABLE 20

| Time (h) | control | AC 4 × MIC | AC 4 × MIC Cineol 16 mg/L | AC4 × MIC Cineol 4 mg/L | Cineol 16 mg/L | Cineol 4 mg/L |
|---|---|---|---|---|---|---|
| 0 | $1.24^E + 07$ | $5.50^E + 02$ | $2.90^E + 02$ | $1.50^E + 02$ | $9.00^E + 06$ | $8.00^E + 06$ |
| 1 | $9.30^E + 06$ | $1.18^E + 03$ | $5.50^E + 02$ | $3.00^E + 02$ | $1.64^E + 07$ | $1.50^E + 07$ |
| 2 | $2.74^E + 07$ | $1.19^E + 03$ | $4.60^E + 02$ | $<10^E 01$ | $5.50^E + 06$ | $1.78^E + 07$ |
| 3 | $3.60^E + 07$ | $3.50^E + 03$ | $3.40^E + 02$ | $3.90^E + 02$ | $7.50^E + 07$ | $5.60^E + 07$ |
| 4 | $2.16^E + 07$ | $8.10^E + 03$ | $1.59^E + 03$ | $1.80^E + 03$ | $5.90^E + 08$ | $7.30^E + 08$ |
| 5 | $2.00^E + 08$ | $9.60^E + 04$ | $2.30^E + 03$ | $3.10^E + 03$ | $3.42^E + 08$ | $3.44^E + 08$ |

TABLE 20-continued

| Time (h) | control | AC 4 × MIC | AC 4 × MIC Cineol 16 mg/L | AC4 × MIC Cineol 4 mg/L | Cineol 16 mg/L | Cineol 4 mg/L |
|---|---|---|---|---|---|---|
| 6 | $2.50^E + 08$ | $3.40^E + 04$ | $1.32^E + 04$ | $1.40^E + 04$ | $5.70^E + 08$ | $5.30^E + 08$ |
| 24 | $3.70^E + 08$ | $4.50^E + 08$ | $4.60^E + 08$ | $2.30^E + 08$ | $9.70^E + 08$ | $9.30^E + 08$ |

Control=absence of cineol and Augmentin®

It is noticed that the addition of cineol enables the number of bacteria to be significantly reduced, including after contacting.

EXAMPLE 5

Resistance

One hundred µl of a Hinton Mueller broth culture of the strain to be investigated (heavy inoculum>$10^{10}$ UFC/ml) are spread on a Mueller Hinton dish containing an oil concentration equal to 4 times the MIC of the product to be tested. After 48 h incubation, the presence or absence of colonies likely to be resistant mutants is observed.

It has been noticed that the use of cineol also enables the occurrence of resistance bacteria to be decreased.

The results are reported in the following tables:

TABLE 21

| Strain 10168/MRSA | |
|---|---|
| ED control | DMSO control |
| invaded | invaded |
| Ciprofloxacin DMSO | Ciprofloxacin/cineol 1:1.5 DMSO |
| invaded | 0 |

Whereas ciprofloxacin alone on methicillin-resistant *S. aureus* (MRSA) causes the occurrence of numerous mutants, the addition of cineol to ciprofloxacin does not cause the occurrence of mutants.

TABLE 22

| Strain 9003/BLSE | |
|---|---|
| ED control | DMSO control |
| invaded | invaded |
| Ciprofloxacin DMSO | Ciprofloxacin/cineol 1:1.5 DMSO |
| Numerous | 26 |

Once again, cineol causes a decrease in the occurrence of mutants on a resistant gram negative strain.

EXAMPLE 6

Sepsis Model

200 µL of a bacterial solution (MRSA) adjusted to 5.108 UFC/ml is injected by the intravenous route (retro-orbital route) to CD1 mice. The treatment is initiated 1 h after the bacteria injection by the subcutaneous route.

At 24 h, the mice are euthanized and a bacterial count is made in the kidney.

In vivo test 1: amoxicillin: clavulanic acid (AMC) injection at variable doses (0.25 mg/kg, 2 mg/kg, 16 mg/kg and 128 mg/kg)+cineol (B) at a constant dose (30 mg/kg), injected 2 times per 24 (H+1 and H+4). Controls: untreated group and group receiving 30 mg/kg cineol without antibiotic. Number of bacteria log10 UFC/g kidney.

Figure 3:
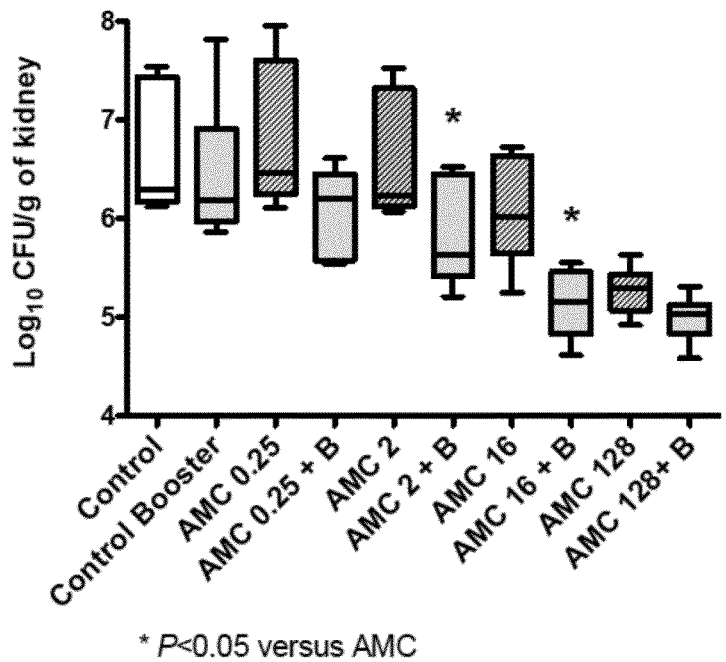
FIG. 3 presents the results of the sepsis model, *In vivo* test 1 of Example 6.

The results are reported in FIG. 3.

In vivo test 2: amoxicillin: clavulanic (AMC) injection at a constant dose (8 mg/kg)+cineol (B) at variable doses (4 mg/kg, 64 mg/kg, 128 mg/kg, 256 mg/kg, 512 mg/kg) injected 2 times a day. Controls: untreated group, group receiving 32 mg/kg cineol without antibiotic (CIN), group receiving 8 mg/kg antibiotic without cineol (AMC8).

(*) $p<0.05$ vs control, AMC8 and CIN
(£) $p<0.05$ vs control and CIN
($) $p<0.05$ vs control, AMC8, CIN, AMC+CIN 128, AMC+CIN 256

Figure 4:
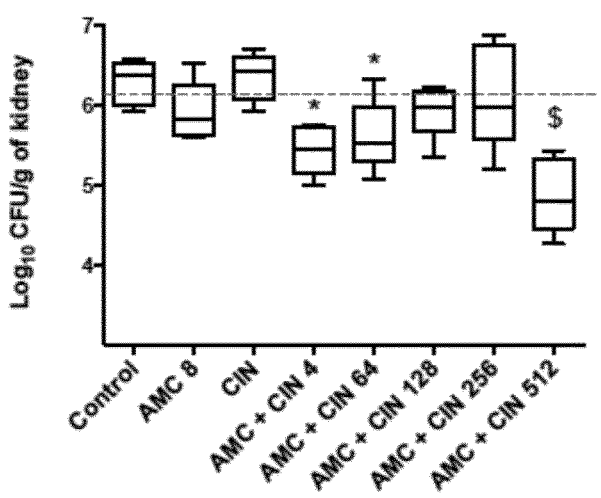
FIG. 4 presents the results of the sepsis model, *In vivo* test 2 of Example 6.

The results are reported in FIG. 4 and also in the following table:

TABLE 23

| Therapeutic regimen | Mean ± SD log10 UFC/g kidney |
|---|---|
| Control | 6.27 ± 0.27 |
| AMC, 8 mg/kg | 5.92 ± 0.36 |
| CIN, 32 mg/kg | 6.35 ± 0.29 |
| AMC + CIN, 4 mg/kg | 5.42 ± 0.32* |
| AMC + CIN, 64 mg/kg | 5.61 ± 0.44 £ |
| AMC + CIN, 128 mg/kg | 5.90 ± 0.32 |
| AMC + CIN, 256 mg/kg | 6.06 ± 0.64 |
| AMC + CIN, 512 mg/kg | 4.87 ± 0.47 $ |

It is again noticed a low dose or high dose potentiation, without potentiating in between the interval. This is in line with the in vitro results which surprisingly demonstrate that the synergy with cineol appears at a low dose (and compatible with the medical use) and at very high doses (incompatible with the medical use). In between these dose extrema, and as has been the case in vitro, a concentration range in which the potentiating effect is absent surprisingly occurs.

EXAMPLE 7

Plasma Antibacterial Efficiency

To Balb/c mice, is injected (Sc.) the antimicrobial product or the antimicrobial+booster mixture. The doses administrated are the following ones:

Group 1: 6 mg/kg gentamycin (GE)
Group 2: 6 mg/kg gentamycin+30 mg/kg cineol
Group 3: amoxicillin (AMX) 30 mg/kg
Group 4: 30 mg/kg amoxicillin+30 mg/kg cineol
Group 5: 30 mg/kg Augmentin® (AMC)
Group 6: 30 mg/kg Augmentin®+30 mg/kg cineol.

At different post-injection times, the mice are euthanised, and blood sampled, heparined and centrifuged to extract plasma thereof A series of successive dilutions (⅓) of the plasma is made and a drop of these different plasma concentrations is deposited onto a seeded Baird Parker medium (MSSA 8238 for groups GE and AMX, MRSA 10168 for the group AMC).

Antibacterial effects are measured after 24 h incubation. The successive dilutions enable the antimicrobial effect to be determined and compared with the MIC. The efficient concentration/MIC ratio is thus determined.

The results are reported in the following tables:

TABLE 24

| c/MIC | 0.083 h | 1 h | 2 h | 5 h | 8 h | 24 h | AUC 0-24 h | Time spent beyond the MIC |
|---|---|---|---|---|---|---|---|---|
| Group 1 average | 10 | 3 | 4 | 0.2 | 0.2 | 0.155 | 19.2005 | <5 h |
| Group 2 average | 2 | 5.4 | 1.5 | 12.65 | 1.15 | 2 | 73.9679 | >24 h |
| Group 3 average | 25 | 3.5 | 2.45 | 0.1505 | 0.5005 | 0.3 | 27.3235 | <5 h |
| Group 4 average | 30 | 7 | 1.95 | 1.2 | 0.95 | 1.1 | 45.7895 | >24 h |

TABLE 25

| | 0.25 h | 0.5 h | 1 h | 2 h | 4 h | 8 h | 24 h | AUC 0-24 h | Time spent beyond the MIC |
|---|---|---|---|---|---|---|---|---|---|
| Group 5 average | 5.5 | 1.75 | 2.15 | 1.75 | 0.3 | 0.3 | 0.01 | 9.56125 | <4 h |
| Group 6 average | 6.5 | 2 | 1.65 | 3.15 | 2 | 1.15 | 1.1 | 33.825 | >24 h |

The plasma concentration to MIC ratio is obtained by the successive dilutions of the plasma. Although this method is semi-quantitative, it however makes it possible to show that the effect is more intense when cineol is present (higher AUC). Furthermore and univocally, the addition of cineol enables the time spent beyond the MIC to be extended.

This result is in line with the curve of FIG. 2, made in vitro.

LIST OF ABBREVIATIONS:

Amox amoxicillin
Aug Augmentin®
Staph *Staphylococcus*
Coli *E. coli*
Pyo *Pseudomonas aeruginosa*
AUC area under the curve

The invention claimed is:

1. A method for treating and/or delaying the onset of clinic signs or symptoms of and/or inhibiting the severity of clinic signs or symptoms associated with a microbial infection in a subject, comprising co-administrating systemically in the subject in need thereof an antimicrobial agent and cineol,
   in a cineol: antimicrobial agent mass ratio, ranging from 8:1 to 1:10,
   in that the antimicrobial agent is not a terpenoid or a phenylpropanoid,
   in that the microbial infection is induced in particular by a strain A pathogen and, in that the concentration [C] of cineol to be used on said strain A is inferior to [MIC]/x, wherein [MIC] is the minimum inhibitory concentration of cineol alone measured on said strain A, with x≥100 and up to 50,000.

2. The method according to claim 1, wherein x is higher than or equal to 1000.

3. The method according to claim 1, wherein x is between 2000 and 10,000.

4. The method according to claim 1, wherein said antimicrobial is an antibiotic.

5. The method according to claim 1, wherein said antimicrobial is an antibiotic chosen from: peptidoglycan synthesis inhibiting antibiotics, nucleic acid synthesis inhibiting antibiotics, folate synthesis inhibiting antibiotics, mycolic acid synthesis inhibiting antibiotics, any of their pharmaceutically acceptable salts, and any of their combinations.

6. The method according to claim 1, wherein the antimicrobial is an antifungal.

7. The method according to claim 1, wherein the antimicrobial is an antifungal chosen from: polyenes, azoles, allylamines, thiocarbamates, echinocandins, griseofulvin, and fluorocytosine.

8. The method according to claim 1, wherein the cineol: antimicrobial agent mass ratio ranges from 4:1 to 1:10.

9. The method according to claim 1, wherein the cineol: antimicrobial agent mass ratio ranges from 1:1 to 1:10.

10. The method according to claim 1, wherein the cineol: antimicrobial agent mass ratio ranges from 1:1 to 1:5.

11. The method according to claim 1, wherein the microbial infection is induced by a pathogen chosen from the following potentially pathogenic genera: *Acetobacter, Acetobacterium, Acinetobacter, Citrobacter, Enterobacter, Enterococcus, Escherichia, Helicobacter, Klebsiella, Proteus, Providencia, Pseudomonas, Salmonella, Serratia, Staphylococcus, Streptococcus, Actinobacillus, Neisseria, Mannheima, Pasteurella, Candida, Aspergillus, Cryptococcus Trichosporon, Malassezia,* and *Mycobacterium*.

12. The method according to claim 1, wherein the antimicrobial is amoxicillin.

13. The method according to claim 1, wherein the antimicrobial is an amoxicillin/clavulanic acid mixture.

14. The method according to claim 1, wherein the antimicrobial is sertaconazole.

* * * * *